United States Patent [19]
Lauwereys et al.

[11] Patent Number: 5,585,259
[45] Date of Patent: Dec. 17, 1996

[54] ECOTIN AS A FACTOR XA, XIA, AND XIIA INHIBITOR

[75] Inventors: Marc J. Lauwereys, Haaltert; Anne-Marie V. R. Lambeir, Oud-Heverlee, both of Belgium

[73] Assignee: Corvas International, Inc., San Diego, Calif.

[21] Appl. No.: 165,304

[22] Filed: Dec. 10, 1993

Related U.S. Application Data

[63] Continuation-in-part of Ser. No. 988,984, Dec. 11, 1992, abandoned.

[51] Int. Cl.$^6$ ............ A61K 38/55; C07K 14/245; C12N 9/50; C12N 9/64
[52] U.S. Cl. ............ 435/226; 435/212; 435/252.1; 514/2; 514/12; 530/350; 530/825; 930/250
[58] Field of Search ................... 435/212, 213, 435/226, 252.1; 514/12, 2; 530/350, 384, 825; 930/250

[56] References Cited

PUBLICATIONS

Chung, C. H. et al. *J. Biol. Chem.* 258:11032–11038 (1983).
McGrath, M. E. et al. *J. Mol. Biol.* 222:139–142 (1991).
Seymour, Jana L., et al.: "Ecotin Is a Potent Anticoagulant and Reversible Tight–Binding Inhibitor of Factor Xa", *Biochemistry* 33:3949–3958 (1994).
Kurz et al., *Thrombosis Research* 60:269–280 (1990), "Rat Model of Arterial Thrombosis Induced by Ferric Chloride".
*Remington's Pharmaceutical Sciences*, Mack Publishing Co. (A. R. Genarro, editor) (1985).

*Primary Examiner*—Dian C. Jacobson
*Attorney, Agent, or Firm*—Lyon & Lyon

[57] ABSTRACT

Pharmaceutical composition containing Ecotin in a therapeutically effective amount for inhibition of blood coagulation.

1 Claim, 5 Drawing Sheets

FIG. 1A

GAATTCGAGC TCGAGCTTAC TCCCCATCCC CCTGTTGACA ATTAATCATC GGCTCGTATA
<u>EcoRI</u>                                    -35                              -10

ATGTGTGGAA TTGTGAGCGG ATAACAATTT CACACAGGAA ACAGGATCCG CGGATCCGTG
                                                      <u>BamHI</u>      <u>BamHI</u>

GAGAAAATAA A ATG AAA CAA AGC ACT ATT GCA CTG GCA CTC TTA CCG TTA
<u>SD</u>         Met Lys Gln Ser Thr Ile Ala Leu Ala Leu Leu Pro Leu

CTG TTT ACC CCT GTG ACA AAA GCG GTACCCGGGG ATCCTCTAGA GTCGACCTGC
Leu Phe Thr Pro Val Thr Lys Ala <u>KpnI</u>

AGGCATGCAA <u>GCTTGGTCTA GA</u>
           <u>HindIII</u>   <u>XbaI</u>

FIG. 1B

```
               10          20          30          40          50
                *           *           *           *           *
GC GAC ATC ATC GGT GGG ATC CTA TAA ATG AAG AAG GAA AGC AAA AAA ATG AAG ACC ATT
                         BamHI                                   Met Lys Thr Ile 60          70          80          90         100         110
        *           *           *           *           *           *
CTA CCT GCA GTA TTG TTT GCC GCT TTC GCT ACC ACT TCC GCC TGG GCG GCA GAA AGC GTC
    PstI
Leu Pro Ala Val Leu Phe Ala Ala Phe Ala Thr Thr Ser Ala Trp Ala Glu Ser Val 120         130         140         150         160         170
        *           *           *           *           *           *
CAG CCA CTG GAA AAA ATC GCG CCT TAT CCA CAA GCT GAA AAA GGG ATG AAG CGT CAG GTG
Gln Pro Leu Glu Lys Ile Ala Pro Tyr Pro Gln Ala Glu Lys Gly Met Lys Arg Gln Val 180         190         200         210         220         230
        *           *           *           *           *           *
ATT CAG TTA ACC CCG CAA GAA GAT GAA TCT ACC CTG AAA GTA GAA CTG TTA ATC GGT CAG
Ile Gln Leu Thr Pro Gln Glu Asp Glu Ser Thr Leu Lys Val Glu Leu Leu Ile Gly Gln
```

```
240
 *
ACG CTG GAA GTC GAT TGC AAT TTG CAT CGT CTC GGC GGG AAG CTG GAA AAC AAA ACG CTG
Thr Leu Glu Val Asp Cys Asn Leu His Arg Leu Gly Gly Lys Leu Glu Asn Lys Thr Leu
            250         260         270         280         290
             *           *           *           *           *

GAA GGC TGG GGC TAT GAT TAT TAT GTC TTT GAT AAA GTC AGT TCC CCG GTT TCA ACG ATG
Glu Gly Trp Gly Tyr Asp Tyr Tyr Val Phe Asp Lys Val Ser Ser Pro Val Ser Thr Met
300         310         320         330         340         350
 *           *           *           *           *           *

ATG GCC TGC CCG GAT GGC AAG AAA GAG AAA TTT GTC ACC GCG TAT CTG GGC GAT GCT
Met Ala Cys Pro Asp Gly Lys Lys Glu Lys Lys Phe Val Thr Ala Tyr Leu Gly Asp Ala
360         370         380         390         400         410
 *           *           *           *           *           *

GGA ATG CTG CGT TAC AAC AGC AAG CTG CCG ATC GTG GTG TAT ACG CCA GAC AAT GTA GAT
Gly Met Leu Arg Tyr Asn Ser Lys Leu Pro Ile Val Val Tyr Thr Pro Asp Asn Val Asp
420         430         440         450         460         470
 *           *           *           *           *           *

GTG AAG TAC CGC GTC TGG AAG GCG GAA GAG AAA ATT GAC AAC GCG GTA GTT CGC TAA GCT
Val Lys Tyr Arg Val Trp Lys Ala Glu Glu Lys Ile Asp Asn Ala Val Val Arg ***
480         490         500         510         520         530  HindIII
 *           *           *           *           *           *

540
 *
TCC GTG AAG TGC
```

ECOTIN AS A FACTOR XA, XIA, AND XIIA INHIBITOR

This application is a continuation-in-part of U.S. Ser. No. 07/988,984, "Ecotin As A Factor Xa Inhibitor", filed Dec. 11, 1992, pending in the Patent Office, now abandoned, and hereby incorporated by reference herein, including the drawings attached thereto.

FIELD OF THE INVENTION

The present invention relates to pharmaceutical compositions including Ecotin, as well as methods for use of Ecotin as a factor Xa, XIa and XIIa inhibitor.

BACKGROUND OF THE INVENTION

Ecotin is a known serine protease inhibitor. The gene encoding this protein has been cloned, and the enzyme's properties characterized. The following is a brief summary of the known features of Ecotin:

Chung et al., 258 *J. Biol. Chem.* 11032, 1983, describe purification of a periplasmic protein, which they termed Ecotin, that is a potent inhibitor of pancreatic proteases, such as chymotrypsin, pancreatic elastase, rat mast cell chymase, and human serosal urokinase. The inhibitor does not inhibit human pulmonary tryptase, kallikrein, papain, pepsin, *Staphylococcus aureus* V8 protease, subtilisin, and thermolysin. Further, it does not inhibit any of the eight soluble endoproteases which are isolated from *E. coli* (including the proteases Do, Re, Mi, Fa, So, La, Ci, and Pi), nor the chymotrypsin-like (protease I) and trypsin-like (protease II) esterases in *E. coli*.

Palmer and St. John, 169 *J. Bacteriology* 1474, 1987, describe three membrane-associated serine proteases that are insensitive to inhibition by Ecotin, despite those proteolytic activities being present in *E. coli*.

McGrath et al., 266 *J. Biol. Chem.* 6620, 1991, describe Ecotin as an unusual serine protease inhibitor since it is able to inhibit chymotrypsin, trypsin and elastase.

McGrath et al., 222 *J. Molecular Biol.* 139, 1991, describes expression of Ecotin in the *E. coli* periplasm, using the endogenous signal peptide and the heterologous tac promoter.

Lee et al., 287 *FEBS Letters* 53, 1991, describe a nucleotide sequence of 876 bases in the *E. coli* chromosome that encodes Ecotin. They proposed that the coding sequence for Ecotin is 486 nucleotides long, and encodes a protein consisting of 162 amino acids.

SUMMARY OF THE INVENTION

Applicant has surprisingly discovered that Ecotin is a potent inhibitor of factor Xa, XIa, and XIIa. Applicant proposes that Ecotin can be used in medical research as an in vitro diagnostic reagent to inhibit the activity of factor Xa, XIa and XIIa. Applicant further proposes that Ecotin can be used as a therapeutic or pharmacological agent by providing Ecotin in a pharmaceutically acceptable buffer in a therapeutic amount within a mammal having an elevated factor Xa activity and/or elevated factor XIa and XIIa activity.

Thus, in a first aspect, the invention features a pharmaceutical composition containing Ecotin in a therapeutically effective amount.

By "Ecotin" is meant that compound or inhibitor described in those publications noted above, and more fully characterized below, and derivatives thereof. Those in the art will recognize that derivatives of Ecotin can be readily formed which have the inhibitory activity of Ecotin for factor Xa, XIa and XIIa but may have slightly altered amino acid sequences. For example, those of ordinary skill in the art can perform routine shotgun mutagenesis, or specific point mutagenesis, using known techniques to create random or defined mutants of Ecotin. Such mutants can be expressed to produce derivatives of Ecotin, and then readily screened for mutants which retain the desired factor Xa, XIa and XIIa inhibitory activities, as described below. Thus, the invention features not only use of Ecotin, but also analogs, homologs, or other equivalent derivatives thereof.

By "pharmaceutical composition" is meant a composition which includes a suitable vehicle for introduction of Ecotin into a human or other mammal in need of an inhibitor of factor Xa, XIa and XIIa.

The present invention also encompasses pharmaceutical compositions prepared for storage and subsequent administration, which have a pharmaceutically effective amount of Ecotin disclosed above in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The compositions of the present invention may be formulated and used as tablets, capsules or elixirs for oral administration; suppositories for rectal administration; sterile solutions, suspensions for injectable administration; and the like. Injectables, which are particularly suited for treatment of blood coagulation, can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The present invention also features a method for preventing or treating a condition in a mammal characterized by an elevated factor Xa level, e.g., abnormal thrombosis or blood coagulation. The pharmaceutically effective amount of the composition required as a dose will depend on the route of administration, the type of animal being treated, and the physical characteristics of the specific animal under consideration. The dose can be tailored to achieve optimal efficacy, but will depend on such factors as weight, diet, concurrent medication and other factors which those skilled in the medical arts will recognize.

In practicing the methods of the invention, the compositions can be used alone or in combination with other effective agents, e.g., in combination with other therapeutic or diagnostic agents. These compounds can be utilized in vivo, ordinarily in a mammal, preferably in a human, or in vitro. In employing them in vivo, the compounds or compositions can be administered to the mammal in a variety of ways, including parenterally, subcutaneously, intramuscularly, colonically, rectally, nasally or intraperitoneally, employing a variety of dosage forms. Most preferably, the material is administered intravenously for treatment of a blood coagulation disorder.

As will be readily apparent to one skilled in the art, the useful in vivo dosage to be administered and the particular mode of administration will vary depending upon the age, weight and mammalian species treated, the particular Ecotin derivative employed, and the specific use for which these derivatives are employed. The determination of effective dosage levels, that is the dosage levels necessary to achieve the desired result, will be within the ambit of one skilled in the art. Typically, applications of compound are commenced at lower dosage levels, with dosage level being increased until the desired effect is achieved.

The dosage for Ecotin of the present invention can range broadly depending upon the desired affects and the therapeutic indication. Typically, dosages will be between about 0.01 μg/kg and 100 mg/kg body weight, preferably between about 0.01 μg/kg and 10 mg/kg body weight. Administration is preferably parenteral, such as intravenous on a daily basis.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIGS. 1A, 1B, 1C show nucleotide sequences used in the construction of pMa5-CI. Specifically, panel (A) shows the relevant part of the recipient vector pMa5-19. The EcoRI/XbaI fragment is present in the multi-cloning site of pMa/c5-8 (Stanssens et al., 17 Nucl. Acids Res. 4441, 1989). The −35 and −10 box of the $P_{tac}$ promoter, the Shine-Dalgarno (SD) sequence and secretion signal derived from the phoA gene as well as some restriction sites are indicated. Panel (B) shows the sequence of the Ecotin-encoding PCR-product obtained with the primers Pst390 and Pst391. The BamHI and HindIII sites used for the directional cloning of the PCR-product in the recipient vector pMa5-19 are shown. The Ecotin secretion signal is underlined.

FIGS. 2A–2B are a diagrammatic representation of the pMa5-CI vector. The map of the pMa5-CI vector contains the following relevant features: (i) a ColE1 type origin of replication (ORI); (ii) the intercistronic region of filamentous phage f1 including the origin of replication (f1-ORI); (iii) the beta-lactamase gene which confers resistance to ampicillin (bla); (iv) the chloramphenicol acetyl transferase gene containing a single point mutation which creates an amber translational stop codon (cat-am); (v) the Ecotin expression module consisting of the IPTG-inducible tac-promoter, the Ecotin gene with its indigenous secretion signal and two copies of the central transcription terminator of phage fd (fdT).

ECOTIN

Applicant surprisingly discovered a factor Xa, XIa, and XIIa inhibitory activity in E. coli lysates. This activity was later identified as Ecotin. The following is an example of the identification of Ecotin as a potent factor Xa, XIa, and XIIa inhibitor, and the processes and procedures by which Ecotin can be isolated, purified and then produced by recombinant DNA techniques. Those of ordinary skill in the art will recognize that these examples are not limiting in the invention, and that they can readily devise equivalent procedures by which Ecotin can be purified or expressed, and then used in factor Xa, XIa, and XIIa assays.

As discussed above, the assays described below can be used to identify derivatives of Ecotin in which a few amino acids are altered, added or deleted, but which retain the Ecotin factor Xa inhibitory activity. Indeed, those experiments can be used to more carefully define the active portion of Ecotin responsible for inhibition of factor Xa, XIa, and XIIa activity. Thus, the invention also features (and the term "Ecotin" includes in its definition) use of smaller derivatives of Ecotin in which one or more amino acid sequences are deleted from the native Ecotin protein.

EXAMPLES

During routine experiments, WK6 E. coli cells harboring a vector, thought to contain a gene coding for a putative factor Xa, XIa, and XIIa inhibitor, were cultured and, after lysis, were found to contain a potent inhibitor for trypsin and factors Xa, XIa and XIIa. The concentration of the inhibitor was estimated by titration of a fixed amount of crude lysate with increasing factor Xa concentrations. The same experiment allows estimation of the inhibition constant of the inhibitor. In a particular experiment, the inhibitor concentration was about 12 nM, and the inhibition constant for factor Xa was in the range of 10 pM.

Subsequently, the inhibitory compound was isolated and found not to be the protein encoded by the vector, but rather a form of the endogenous E. coli trypsin inhibitor know as Ecotin. The presence of a potent factor Xa inhibitor could also be demonstrated in E. coli cells, carrying a different vector. The methods used to measure inhibitor properties, and to purify the inhibitor and characterize the protein are given below.

EXAMPLE 1: Cell Growth and Lysis

Transformed E. coli (WK6, containing vectors thought to express a factor Xa, XIa, and XIIa inhibitor) were grown in 250 ml baffled Erlenmeyers flasks at 37° C. in the presence of ampicillin. The cells were induced after 3 hours by addition of 0.1 mM IPTG and grown overnight.

In one particular procedure the total E. coli soluble fraction was used for the isolation, using the protocol described by Marks et al., 261 J. Biol. Chem. 7115, 1986.

Specifically, about 1 g of wet cell paste was suspended in 1.5 ml 40 mM TRIS buffer pH 8 containing 20% sucrose and 5 mM EDTA. 2.5 mg lysozyme was added, followed by 1.15 ml of 0.1% Triton X-100 and 0.3 ml NaCl (5M). After 15 minutes at room temperature, 2.5 ml of 200 mM TEA buffer pH 7.8 was added followed by 0.15 ml $CaCl_2$ (1M) and 0.1 ml $MgCl_2$ (1M) and 10 μg of DNAseI. The suspension was stirred for 20 minutes at 25° C.

The majority of the protein in the suspension was precipitated by addition of trichloroacetic acid (TCA) to a final concentration of 2%, and aggregates removed by centrifugation. The TCA supernatant was neutralized by the addition of NaOH for further purification.

EXAMPLE 2: Titration of Crude E. coli Lysate with Factor Xa

Figure 4:
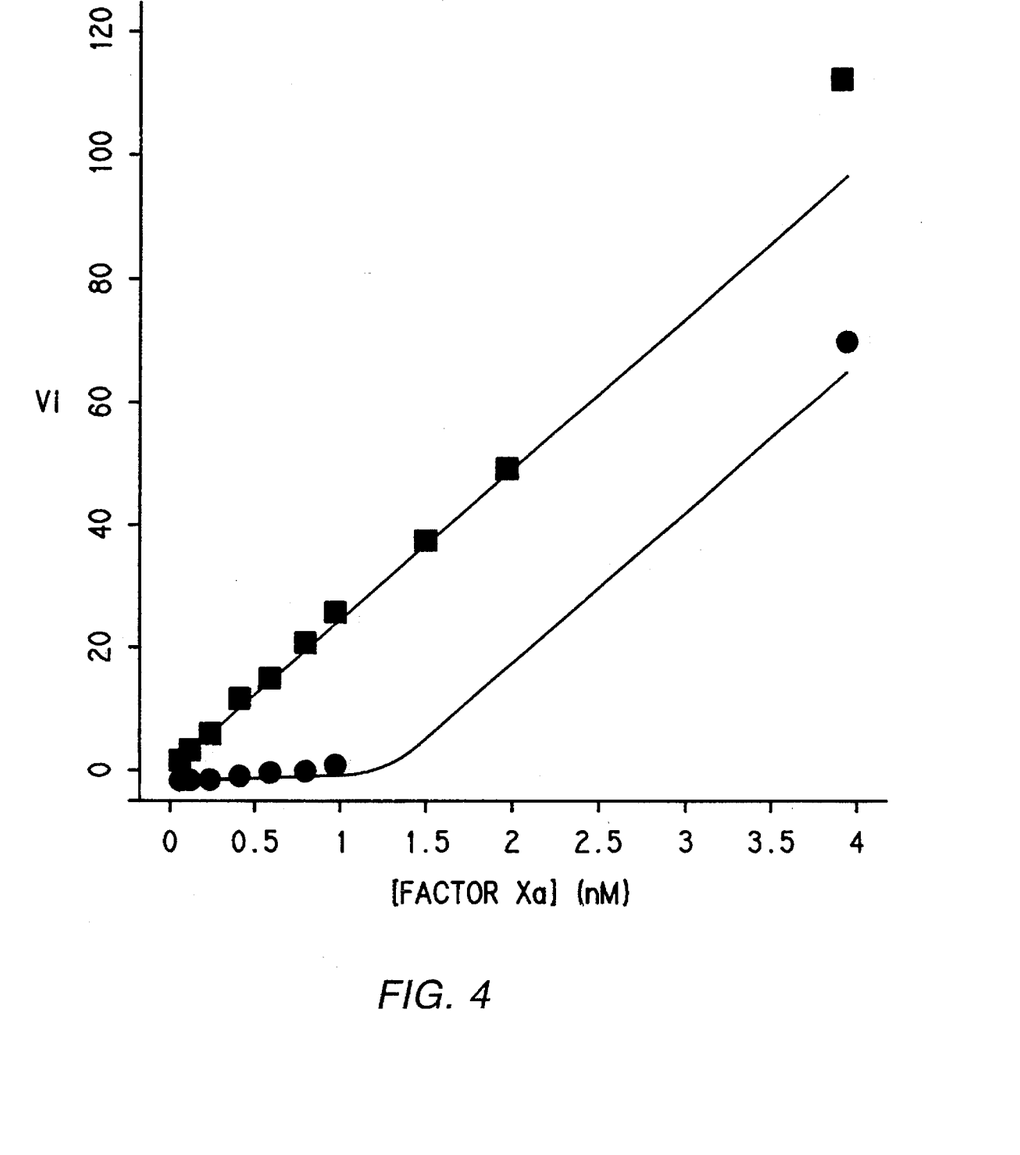
FIG. 4 is a graph showing titration of a 1/20 dilution (circles) of a 2% TCA supernatant of a crude E. coli lysate with factor Xa. Rectangles show the initial rates in absence of inhibitor.

Two percent TCA supernatant was diluted 1/20 and 1/40 in TBSA (100 mM TRIS, 140 mM NaCl pH 7.4, 0.1% BSA), incubated with increasing amounts of factor Xa (0.05–4 nM) during 2 hours at room temperature (about 20° C.) in microtiter plate wells. 0.25 mM factor Xa substrate was added (N—α—Cbo—D—Arg—Gly—Arg—pNa.2HCl) and the initial rate was determined at 405 nM during 40 minutes. The initial rate ($v_i$) was plotted versus the factor Xa concentration ([E]) and fitted with the following equation to give an estimate of the inhibitor concentration ([I]) and the inhibition constant (Ki).

$$v_i = Spa * \{([E]-[I]-K_i) + \sqrt{(([I]+K_i-[E])^2 + 4*Ki*[E])}\}/2$$

Where Spa is the specific activity of factor Xa in the conditions of the assay.

The results of one such experiment are shown in FIG. 4. These results demonstrate a factor Xa inhibitory activity in the TCA supernatant.

EXAMPLE 3: Purification of Factor Xa Inhibitor from TCA Supernatant

Figure 3:
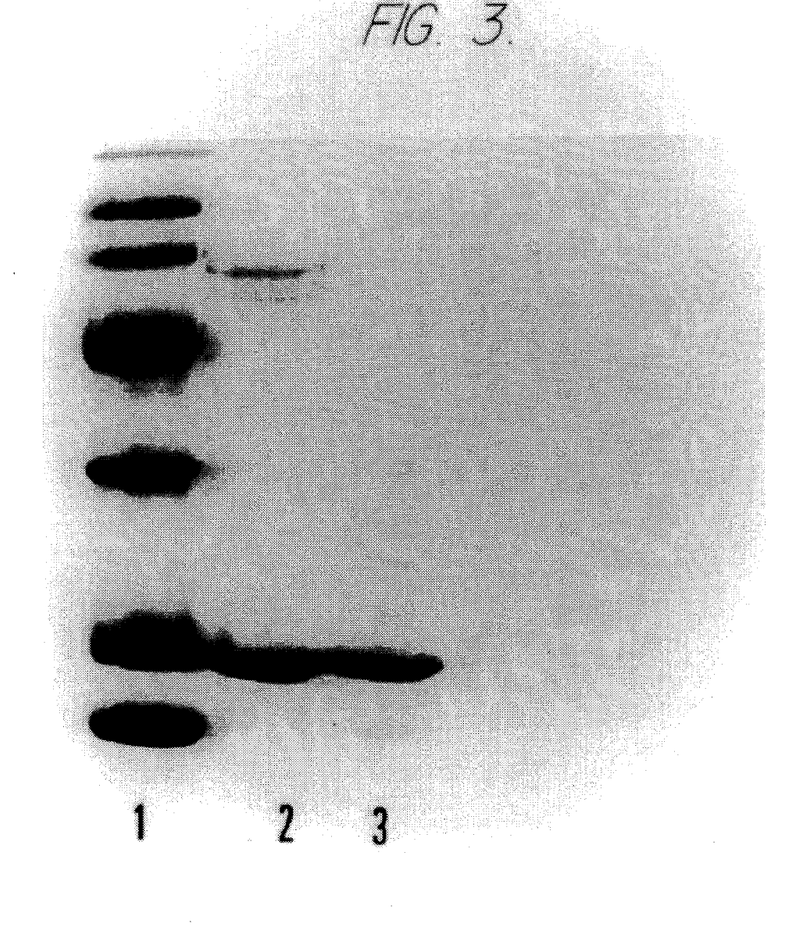
FIG. 3 is a reproduction of an SDS polyacrylamide gel (15% acrylamide) Coomassie Blue stained, showing molecular weight markers in lane 1, factor Xa inhibitory protein from periplasmic fraction in lane 2, and factor Xa inhibitory protein from total lysate in lane 3.

Purification of the inhibitor was achieved by affinity chromatography on Trypsin-Sepharose, equilibrated in 100 mM TEA pH 7.8, 300 mM NaCl, washed with 5 column volumes of 100 mM TEA pH 7.8, 300 mM NaCl and further washed with 5 column volumes of 10 mM TEA pH 7.8, 50 mM NaCl. The adsorbed material was eluted with 20 mM HCl, 50 mM NaCl pH 1.8. The eluted material was further fractionated by reversed phase chromatography on Vydac C18. The column was equilibrated in 0.1% TFA/water solvent, and developed with a linear gradient of increasing acetonitrile from 0 to 50% at a flow rate of 1 ml/min. The fractions containing the inhibitory activity against factor Xa and Trypsin were subjected to SDS-PAGE electrophoresis (see FIG. 3, lane 3) and N-terminal sequence determination (see Example 5).

EXAMPLE 4: Purification of Factor Xa Inhibitor from the E. coli Periplasmic Fraction The inhibitor was also isolated from the periplasmic fraction of WK6 cells containing a vector thought to encode an inhibitor. Specifically, cells harvested from 0.6 L culture were resuspended in 72 ml 10 mM Tris pH 7.5, 20% sucrose, 10 mM EDTA and left for 10 minutes at room temperature before centrifugation. The pellet was subsequently resuspended in 70 ml water. After 10 minutes the supernatant was collected by centrifugation and 4 ml NaCl (5M) and 1.4 ml TEA pH 7.8 was added. After centrifugation the purification was achieved by affinity chromatography on Trypsin-Sepharose, equilibrated in 100 mM TEA pH 7.8, 300 mM NaCl, washed with 5 column volumes of 100 mM TEA pH 7.8, 300 mM NaCl and further washed with 5 column volumes of 10 mM TEA pH 7.8, 50 mM NaCl. The adsorbed material was eluted with 20 mM HCl, 50 mM NaCl pH 1.8. The eluted material was further fractionated by reversed phase chromatography on Vydac C4. The fraction containing the inhibitory activity for factor Xa and Trypsin was subjected to SDS-PAGE and had the same mobility on 15% SDS-PAGE as the protein purified from the total cell lysate (see FIG. 3, lane 2).

EXAMPLE 5: Molecular Weight and N-terminal Sequence Determination

The inhibitor isolated from E. coli cells as described in Example 3, was subjected to automated gas phase Edman degradation for 15 cycles on an Applied Biosystems Sequencer. The deduced N-terminal amino acid sequence Ala—Thr—Thr—Ser—Ala—Trp—Ala—Ala—Glu—Ser—Val—Gln—Pro—Leu—Glu—SEQ ID NO. 5 is in agreement with the published sequence of the E. coli Trypsin inhibitor known as Ecotin. The first seven amino acids (underlined) of the purified material are part of the signal peptide, as deduced from the DNA sequence. McGrath et al., 266 J. Biol. Chem. 6620, 1991.

EXAMPLE 6: Cloning of the Ecotin Gene on the pMa5–19 Vector

The Ecotin gene was isolated from total DNA of E. coli strain WK6 by PCR-technology, and subsequently introduced in the vector pMa5–19 for expression purposes. For the preparation of total E. coli DNA, the cell-pellet of a 40 ml culture was resuspended in 15 ml TE (50 mM Tris pH 8.0, 20 mM EDTA). 5 ml of a proteinase K solution (2.5 mg/ml) was added and the mixture incubated for 2 hours at 37° C. After mixing with 5 ml sarcosyl (5% in TE) and incubation for another hour at 37° C. (until clear), the mixture was extracted twice with 20 ml phenol and three times with ether. DNA was precipitated by the addition of 1/10 volume 5M NaClO$_4$ and 1 volume isopropanol and collected by centrifugation (10,000 rpm, 10 minutes). The pellet was washed with 95% EtOH and resuspended in 4 ml TE. The quality of the material was checked by agarose-gel electrophoresis and the concentration determined spectrophotometrically.

The Ecotin gene, including the presumed secretion signal and ribosome binding site, was amplified using the following oligonucleotide-primers:

Pst 390: 5'-GCGACATCAT.CGGTGGGATC-.CTATAAATGA.AGA SEQ ID NO: 6

BamHI

Pst 391: 5'-GCACTTCACG.GAAGCTTAGC.GAAC-TACCGC SEQ ID NO: 7

HindIII

Note that Pst390 and Pst391 contain a BamHI and HindIII restriction site, respectively, allowing the directional cloning of the obtained PCR product in the chosen expression vector (see below). For PCR-amplification, the following was prepared:

(A): E. coli DNA, 5 ng (1 μl); Pst390, 100 pmoles (1 μl); Pst391, 100 pmoles (1 μl); dNTPs, 20 mM (1 μl); 10×Vent buffer (8 μl); H$_2$O, 68 μl (B): 10×Vent buffer (3 μl), Vent-polymerase, 3 μl of 2 units/μl, H$_2$O, 24 μl.

A 40 μl quantity of (A) was heated to 95° C. after which 10 μl of (B), also heated to 95° C., was added; the resultant mixture was subjected to 25 rounds of temperature cycling: 1 cycle=1 minute at 95° C. (denature), 1 minute at 55° C. (anneal) and 1.5 minutes at 72° C. (elongate). A second mixture of (A) and (B) was subjected to 35 temperature cycles. One-tenth of both PCR reactions was checked on agarose gel: each one the two amplifications gave a prominent band of the expected size (about 550 bp) following ethidium bromide staining. The PCR product resulting from the 35-cycle amplification was isolated from gel and subsequently digested with the enzymes BamHI and HindIII.

Figure 1A:
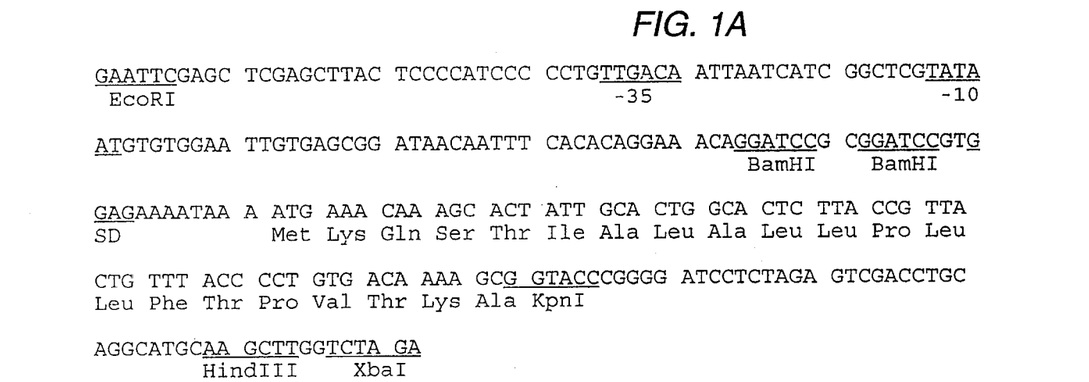
Figure 1B:
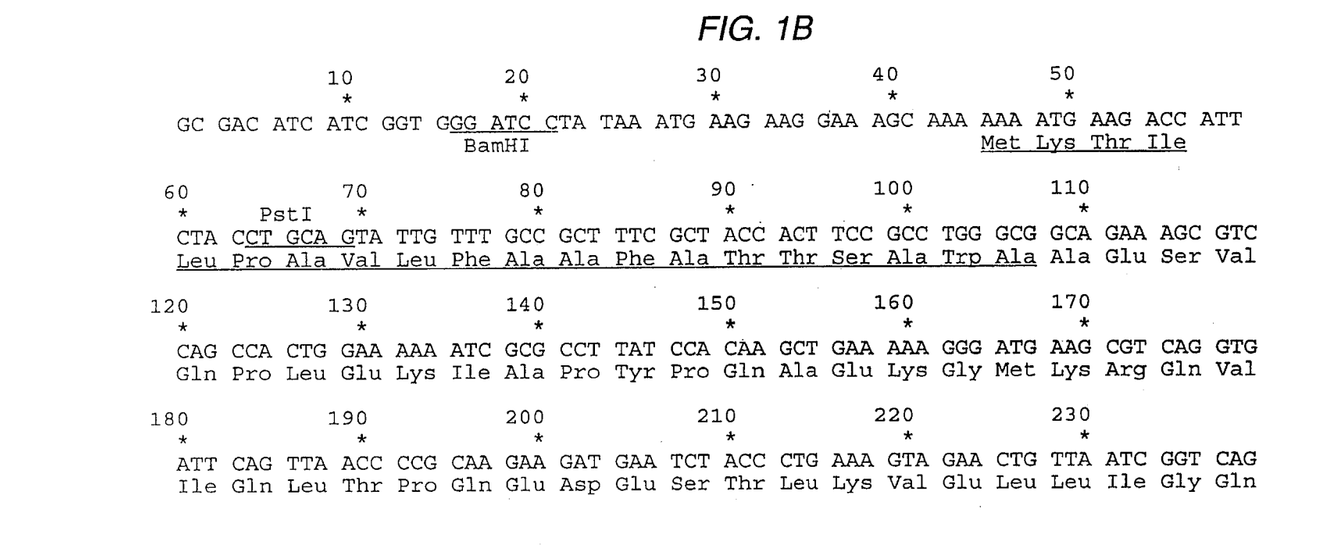
Figure 1C:
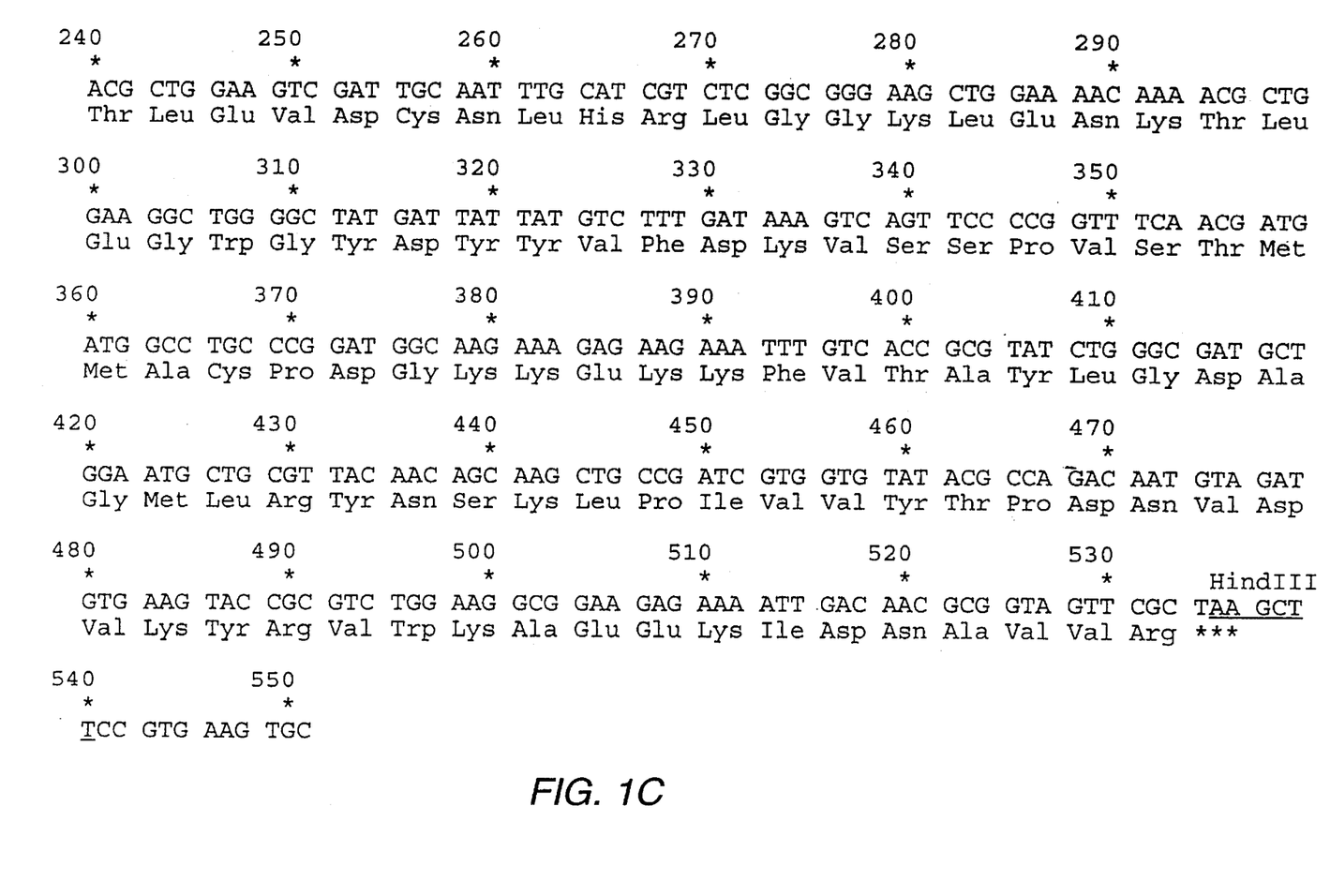
Figure 2A:
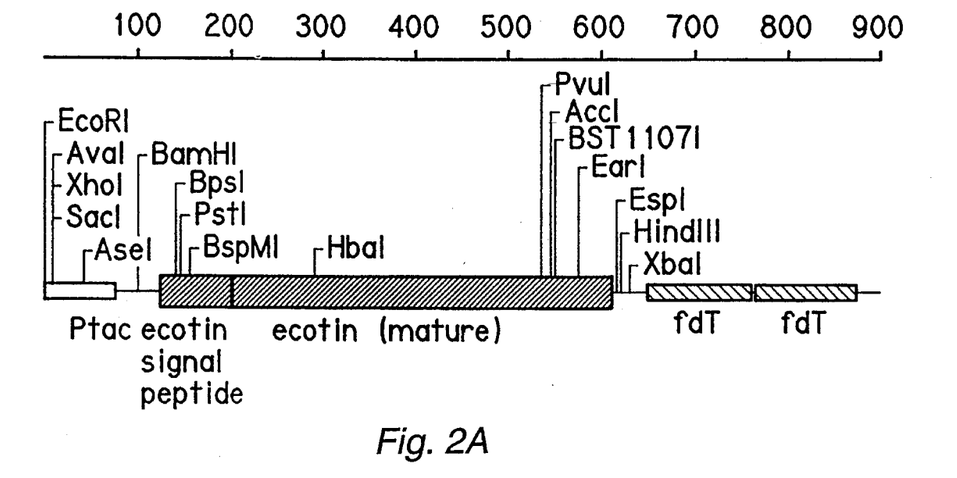
Figure 2B:
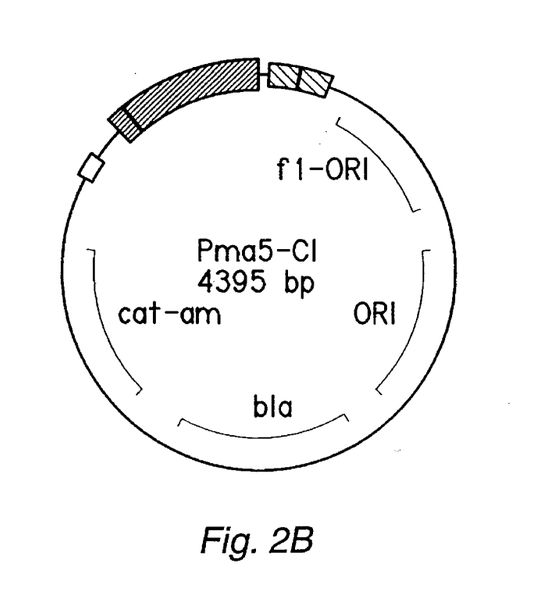

The recipient pMa5-19 plasmid (see FIG. 1) was opened with BamHI and HindIII digestion. The large vector-fragment was purified from agarose gel and ligated with the above-mentioned BamHI/HindIII digested PCR-product. The $lacI^q$ strain WK6 was transformed with the ligation mixture. Twelve randomly picked $Ap^R$ transformants were characterized by restriction analysis; one clone, designated pMa5-CI, was retained (FIG. 2).

The sequence of the entire Ecotin coding region of this clone was found to be in complete agreement with literature publications. Upon derepression of the $P_{tac}$ promoter, WK6 cells, harboring pMa5-CI, were found to direct the synthesis of Ecotin as shown by the dramatic increase in trypsin/factor Xa/elastase inhibitory activity. This activity can be released with an osmotic shock, demonstrating that Ecotin accumulates in the periplasmic space. Production of Ecotin could also be demonstrated by gel-electrophoretic fractionation of total cellular extracts followed by coomassie-staining; the protein profile of an IPTG-induced culture was found to contain a new protein with the expected molecular size. From the activity measurements it can be calculated that the Ecotin protein amounts to about 50 mg per liter culture ($OD_{600\,nm}=\pm 4$). Following purification (see below), the recombinant Ecotin was subjected to N-terminal sequencing. The result is consistent with literature data (Ala—Glu—Ser—Val—Gln—) SEQ ID NO: 8.

EXAMPLE 7: Purification of Recombinant Ecotin

The overexpressed protein was purified from the periplasmic fraction. Cells from 2 L culture were resuspended in 120 ml 10 mM Tris pH 7.5, 20% sucrose, 10 mM EDTA and left for 10 minutes at room temperature before centrifugation. The pellet was subsequently resuspended in 120 ml water. After 10 minutes the supernatant was collected by centrifugation and adjusted to pH 3.4 by the addition of HCl. Precipitated material was removed by centrifugation. Solid NaCl to a final concentration of 0.3M was added and the pH adjusted to 7.4. The liquid was subsequently heated for 30 minutes at 90° C.

Precipitated material was removed by centrifugation. Solid ammonium sulfate (430 g/L) was added and the suspension stored overnight at 4° C. After centrifugation, the pellet was dissolved in water, and the solution fractionated on Superdex 75 (16/60) gel filtration column. The fractions containing Ecotin were pooled and dialyzed extensively against water. Protein concentration was estimated using the calculated extinction coefficient, $\epsilon_{278}=1.47$ for 1.0 mg/ml. The molecular mass is 16,098 Daltons.

EXAMPLE 8: Protease Assays

Protease activity was determined using commercially available chromogenic substrates and purified proteases. The initial rate was determined with a Thermomax (Molecular Devices) microtiterplate reader at 405 nm wavelength at room temperature. The buffer used for all measurements contained 100 mM TRIS, 140 mM NaCl, 0.1% BSA, pH 7.4.

| assayed protease | protease concentration in assay (nM) | substrate | substrate concentration in assay (mM) |
|---|---|---|---|
| factor Xa | 0.68 | N-α-Cbo—D—Arg—Gly—Arg-pNa · 2HCl | 0.25 |
| trypsin | 0.6 | N—Bz—Ile—Glu—(γ-OR)—Gly—Arg-pNA · HCl R = H (50%), CH₃ (50%) | 0.25 |
| thrombin | 2 | H—D—Phe—Pip—Arg-pNA · 2HCl | 0.5 |
| plasma kallikrein | 0.025 nKat/ml | H—D—Pro—Phe—Arg-pNA · 2HCl | 0.4 |
| factor VIIa-tissue factor | 2.5 | H—D—Ile—Pro—Arg-pNA · 2HCl | 0.4 |
| plasmin | 1 | L-pyroglutamyl—Pro—Arg-pNA · HCl | 0.2 |
| elastase | 10 | N-succinyl—Ala—Ala—Ala-pNA | 0.5 |
| factor XIa | 0.5 | H—D—Val—Leu—Arg-pNA | 0.25 |
| factor XIIa | 1 | D-hexahydroTyrosine-Gly—Arg-pNA diacetate | 0.2 |
| aPC | 1 | γ-Cbo—D—Lys—Pro—Arg-pNA diacetate | 0.4 |
| rt-PA | 1 | O-(methylsulfonyl)-D-hexahydroTyrosine-Gly—Arg-pNA acetate | 1 |
| urokinase | 1 | O-(methylsulfonyl)-D-hexahydroTyrosine-Gly—Arg-pNA acetate | 1 | pNA = para-nitrophenylanilide, Cbo = Benzoyloxycarbonyl, Bz = Benzoyl.

To determine inhibition constants, the protease was incubated during 90 minutes (factor Xa), 45 minutes (trypsin), or 30 minutes (thrombin, plasmin, factor VIIa-tissue factor, human plasma kallikrein, porcine pancreatic elastase, factor XIa, factor XIIa, activated protein C, recombinant t-PA and urokinase) in 150 μl before the substrate (50 μl) was added. The inhibition constant was determined from a plot of the relative activity versus the inhibitor concentration fitted with the following equation:

$$v_i/v_o=\{([E_t]-[I_t]-K_i^*)+[([I_t]+_i^*-[E_t])^2+4K_i^*[E_t]]^{1/2}\}/2[E_t]$$

except for thrombin where the total enzyme concentration can be neglected compared to the inhibitor concentration and the equation is reduced to:

$$v_i/v_o=1/(1+[I_t]/K_i^*).$$

$v_i$ and $v_o$ are the initial rates measured in presence and in absence of inhibitor, $[I_t]$ and $[E_t]$ are the total inhibitor and enzyme concentrations and $K_i^*$ is the apparent inhibition constant. It was assumed that under these conditions the apparent inhibition constant is not dependent on the substrate concentration and corresponds to the binding constant of the inhibitor to the active site of the protease in the conditions of the experiment.

The factor VIIa-tissue factor complex was not inhibited by recombinant Ecotin at concentrations up to 1 µM. Plasmin inhibition by 1 µM recombinant Ecotin was 15%. The inhibition constants of recombinant Ecotin for various other proteases are given below.

| Protease | Inhibition constant (nM) |
| --- | --- |
| factor Xa | 0.05–0.2 |
| trypsin | 0.01 |
| thrombin | 7200 |
| human plasma kallikrein | 1.4 |
| factor XIa | 2.5–25 |
| factor XIIA | <<<2.5 |
| chymotrypsin | <<<2.5 |
| plasmin | inactive |
| activated protein C | >>2500 |
| rt-PA | >>2500 |
| urokinase | >>2500 |

EXAMPLE 9 Rat Model of FeCl$_3$-induced Platelet-dependent Arterial Thrombosis The rat model is a well characterized model of platelet dependent, arterial thrombosis which has been used in the evaluation potential antithrombotic compounds such as direct thrombin inhibitors. Kurz et al., 60 *Thromb. Res.* 269, 1990. Thrombus development in this model is relatively heparin insensitive, which suggests that this model may be more representative of the type of thrombosis which has been observed clinically in newly re-canalized coronary vessels following balloon angioplasty or enzymatic thrombolysis. In this model a platelet-rich, occlusive thrombus is formed in a segment of the rat carotid artery treated with a fresh solution of FeCl$_3$ absorbed to a piece of filter paper. The FeCl$_3$ is thought to diffuse into the treated segment of artery and causes de-endothelialization resulting in thrombus formation. The effect of a test compound on the incidence of occlusive thrombus formation following the application of the FeCl$_3$ is monitored by ultrasonic flowtometry, and is used as the primary end point. The use of flowtometry is a modification of the original procedure in which thermal detection of clot formation was employed. Kurz et al., supra.

Male Harlan Sprague Dawley rats (420–450 g) were acclimated at least 72 hours prior to use and fasted for 12 hours prior to surgery with free access to water. The animals were prepared, anesthetized with Nembutal with catheters for blood pressure monitoring, drug and anesthesia delivery being implanted as described above. The left carotid artery was isolated by making a midline cervical incision followed by blunt dissection and spreading techniques to separate a 2 cm segment of the vessel from the carotid sheath. A silk suture was inserted under the proximal and distal ends of the isolated vessel to provide clearance for the placement of an ultrasonic flow probe (Transonic) around the proximal end of the vessel. The probe was then secured with a stationary arm.

Following surgery, the animals were randomized in either a control (saline infusion) or treatment group with test compound (Ecotin) with at least 4 animals per group at the indicated dose. The test compound was administered as a continuous intravenous infusion after placement of the flow probe and stabilization of the preparation for a period of 60 minutes prior to and following application of the FeCl$_3$. At t=0, a 3 mm diameter piece of filter paper (Whatman #3) soaked with 10 µl of a 35% solution of fresh FeCl$_3$ (made up in water) was applied to the segment of isolated carotid artery distal to the flow probe. Blood pressure, blood flow, heart rate, and respiration were monitored for 60 minutes.

The incidence of occlusion (defined as the attainment of zero blood flow) was recorded as the primary end point. Following the 60 minute observation period, the flow probe was removed and the area cleared of all excess fluid. The distal and proximal sutures were tied off and arterial clamps placed on the far proximal and distal ends of the segment. The isolated segment was cut out, blotted dry on filter paper and weighed. The segment was re-weighed following removal of the clot and the difference recorded as total % clot weight. The animals were euthanized as described above.

The efficacy of Ecotin, produced as described above, as an antithrombotic agent in this in vivo model was demonstrated by the reduction in the incidence of occlusion and in clot size, as shown below.

| Treatment Group | Incidence of Occlusion | Time to Occlusion (min) | Clot Formation (%) |
| --- | --- | --- | --- |
| Control (No Treatment) | 4/4 | 16.8 ± 1.3 | 60.83 ± 5.56 |
| Ecotin 10 µg/kg/min | 2/6 | 20.1 ± 0.9 | 12.73 ± 8.04* |

*$p<0.01$ vs Control by ANOVA followed by Newman-Kuels test

Other embodiments are within the following claims.

We claim:

1. Method for inhibiting factor Xa activity, comprising contacting factor Xa with Ecotin.

* * * * *

UNITED STATES PATENT AND TRADEMARK OFFICE
CERTIFICATE OF CORRECTION

PATENT NO. : 5,585,259

DATED : December 17, 1996

INVENTOR(S) : Marc J. Lauwereys, et al.

It is certified that error appears in the above-indentified patent and that said Letters Patent is hereby corrected as shown below:

Column 8, line 55, delete "$V/V_o = \{([E_t] - [I_t] - K_i^*) + [([I_t] + {}_i^* - [E_t])^2 + 4K_i^*[E_t]]^{1/2}\}/2[E_t]$"

and insert --$V/V_o = \{([E_t] - [I_t] - K_i^*) + [([I_t] + K_i^* - [E_t])^2 + 4K_i^*[E_t]]^{1/2}\}/2[E_t]$--

Signed and Sealed this

Fourth Day of November, 1997

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 246
        ( B ) TYPE: nucleic acid
        ( C ) STRANDEDNESS: single
        ( D ) TOPOLOGY: linear     ( i i ) SEQUENCE DESCRIPTION: SEQ ID NO: 1:

```
GAATTCGAGC   TCGAGCTTAC   TCCCCATCCC   CCTGTTGACA   ATTAATCATC   GGCTCGTATA            6 0
```

-continued

| | | | | |
|---|---|---|---|---|
| ATGTGTGGAA | TTGTGAGCGG | ATAACAATTT | CACACAGGAA | ACAGGATCCG CGGATCCGTG | 120 |
| GAGAAAATAA | AATGAAACAA | AGCACTATTG | CACTGGCACT | CTTACCGTTA CTGTTTACCC | 180 |
| CTGTGACAAA | AGCGGTACCC | GGGGATCCTC | TAGAGTCGAC | CTGCAGGCAT GCAAGCTTGG | 240 |
| TCTAGA | | | | | 246 |

( 2 ) INFORMATION FOR SEQ ID NO: 2:

( i ) SEQUENCE CHARACTERISTICS:
        ( A ) LENGTH: 21
        ( B ) TYPE: amino acid
        ( C ) TOPOLOGY: linear     ( i i ) SEQUENCE DESCRIPTION: SEQ ID NO: 2:

```
Met Lys Gln Ser Thr Ile Ala Leu Ala Leu Leu Pro Leu Leu Phe Thr
                 5                  10                  15
Pro Val Thr Lys Ala
             20
```

( 2 ) INFORMATION FOR SEQ ID NO: 3:

( i ) SEQUENCE CHARACTERISTICS:
        ( A ) LENGTH: 551
        ( B ) TYPE: nucleic acid
        ( C ) STRANDEDNESS: single
        ( D ) TOPOLOGY: linear     ( i i ) SEQUENCE DESCRIPTION: SEQ ID NO: 3:

| | | | | | |
|---|---|---|---|---|---|
| GCGACATCAT | CGGTGGGATC | CTATAAATGA | AGAAGGAAAG | CAAAAAAATG AAGACCATTC | 60 |
| TACCTGCAGT | ATTGTTTGCC | GCTTTCGCTA | CCACTTCCGC | CTGGGCGGCA GAAAGCGTCC | 120 |
| AGCCACTGGA | AAAAATCGCG | CCTTATCCAC | AAGCTGAAAA | AGGGATGAAG CGTCAGGTGA | 180 |
| TTCAGTTAAC | CCCGCAAGAA | GATGAATCTA | CCCTGAAAGT | AGAACTGTTA ATCGGTCAGA | 240 |
| CGCTGGAAGT | CGATTGCAAT | TTGCATCGTC | TCGGCGGGAA | GCTGGAAAAC AAAACGCTGG | 300 |
| AAGGCTGGGG | CTATGATTAT | TATGTCTTTG | ATAAAGTCAG | TTCCCCGGTT TCAACGATGA | 360 |
| TGGCCTGCCC | GGATGGCAAG | AAAGAGAAGA | AATTTGTCAC | CGCGTATCTG GGCGATGCTG | 420 |
| GAATGCTGCG | TTACAACAGC | AAGCTGCCGA | TCGTGGTGTA | TACGCCAGAC AATGTAGATG | 480 |
| TGAAGTACCG | CGTCTGGAAG | GCGGAAGAGA | AAATTGACAA | CGCGGTAGTT CGCTAAGCTT | 540 |
| CCGTGAAGTG | C | | | | 551 |

( 2 ) INFORMATION FOR SEQ ID NO: 4:

( i ) SEQUENCE CHARACTERISTICS:
        ( A ) LENGTH: 162
        ( B ) TYPE: amino acid
        ( C ) TOPOLOGY: linear     ( i i ) SEQUENCE DESCRIPTION: SEQ ID NO: 4:

```
Met Lys Thr Ile Leu Pro Ala Val Leu Phe Ala Ala Phe Ala Thr Thr
                 5                  10                  15
Ser Ala Trp Ala Ala Glu Ser Val Gln Pro Leu Glu Lys Ile Ala Pro
             20                  25                  30
Tyr Pro Gln Ala Glu Lys Gly Met Lys Arg Gln Val Ile Gln Leu Thr
         35                  40                  45
Pro Gln Glu Asp Glu Ser Thr Leu Lys Val Glu Leu Leu Ile Gly Gln
     50                  55                  60
Thr Leu Glu Val Asp Cys Asn Leu His Arg Leu Gly Gly Lys Leu Glu
65                  70                  75                  80
```

```
Asn Lys Thr Leu Glu Gly Trp Gly Tyr Asp Tyr Tyr Val Phe Asp Lys
                 85                  90                   95
Val Ser Ser Pro Val Ser Thr Met Met Ala Cys Pro Asp Gly Lys Lys
            100             105                     110
Glu Lys Lys Phe Val Thr Ala Tyr Leu Gly Asp Ala Gly Met Leu Arg
        115                 120                 125
Tyr Asn Ser Lys Leu Pro Ile Val Val Tyr Thr Pro Asp Asn Val Asp
    130                 135                 140
Val Lys Tyr Arg Val Trp Lys Ala Glu Glu Lys Ile Asp Asn Ala Val
145                 150                 155                 160
Val Arg
```

( 2 ) INFORMATION FOR SEQ ID NO: 5:

( i ) SEQUENCE CHARACTERISTICS:
        ( A ) LENGTH: 15
        ( B ) TYPE: amino acid
        ( C ) TOPOLOGY: linear     ( i i ) SEQUENCE DESCRIPTION: SEQ ID NO: 5:

```
Ala Thr Thr Ser Ala Trp Ala Ala Glu Ser Val Gln Pro Leu Glu
                5                   10                  15
```

( 2 ) INFORMATION FOR SEQ ID NO: 6:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear     ( i i ) SEQUENCE DESCRIPTION: SEQ ID NO: 6:

GCGACATCAT CGGTGGGATC CTATAAATGA AGA      33

( 2 ) INFORMATION FOR SEQ ID NO: 7:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear     ( i i ) SEQUENCE DESCRIPTION: SEQ ID NO: 7:

GCACTTCACG GAAGCTTAGC GAACTACCGC      30

( 2 ) INFORMATION FOR SEQ ID NO: 8:

( i ) SEQUENCE CHARACTERISTICS:
        ( A ) LENGTH: 5
        ( B ) TYPE: amino acid
        ( C ) TOPOLOGY: linear     ( i i ) SEQUENCE DESCRIPTION: SEQ ID NO: 8:

```
Ala Glu Ser Val Gln
                5
```